(12) United States Patent
McEwen et al.

(10) Patent No.: US 6,729,552 B1
(45) Date of Patent: May 4, 2004

(54) LIQUID DISPERSION DEVICE

(75) Inventors: Charles Nehemiah McEwen, Newark, DE (US); William J. Herron, Newark, DE (US); Richard G. McKay, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/420,142

(22) Filed: Apr. 22, 2003

(51) Int. Cl.$^7$ .............................. A24F 25/00; A61L 9/04
(52) U.S. Cl. .............................. 239/49; 239/44; 239/37
(58) Field of Search .............................. 239/690, 37, 38, 239/43, 44, 45, 46, 49, 51, 57, 697, 698, 135, 136, 690.1, 691, 692, 693, 694, 695, 696, 699

(56) References Cited

U.S. PATENT DOCUMENTS

| | | | |
|---|---|---|---|
| 2,942,090 A | | 6/1960 | Diehl |
| 3,780,260 A | | 12/1973 | Elsner |
| 4,084,079 A | | 4/1978 | Costello |
| 4,346,059 A | * | 8/1982 | Spector .............. 422/125 |
| 5,238,187 A | | 8/1993 | Zlotnik et al. |
| 5,503,335 A | * | 4/1996 | Noakes et al. .............. 239/690 |
| 5,647,053 A | | 7/1997 | Schroeder et al. |
| 5,810,265 A | | 9/1998 | Cornelius et al. |
| 6,104,867 A | | 8/2000 | Stathakis et al. |
| 6,144,801 A | * | 11/2000 | Lehoux et al. .............. 392/390 |
| 6,297,499 B1 | | 10/2001 | Fenn |
| 6,478,440 B1 | | 11/2002 | Jaworski et al. |
| 2002/0155026 A1 | | 10/2002 | Lins |

FOREIGN PATENT DOCUMENTS

| | | |
|---|---|---|
| EP | 0 195 548 A2 | 9/1986 |
| EP | 0 523 962 A1 | 1/1993 |
| EP | 1 010 468 A1 | 6/2000 |
| EP | 0 486 198 B1 | 2/2001 |
| WO | WO 0038512 A1 | 7/2000 |
| WO | WO 0139809 A1 | 6/2001 |

* cited by examiner

*Primary Examiner*—Thomas Denion
*Assistant Examiner*—Jaime Corrigan

(57) ABSTRACT

A device that can be used for dispersing a liquid is disclose. The device comprises a container, a capillary device, and a housing. The container has an open end that is connected to the capillary device and comprises a liquid. The capillary device comprises a substantially tubular member having one end secured to the open end of the container and the opposing end extended therethrough a substantially tubular capillary structure, which is coaxially aligned with the substantially tubular member. The capillary structure is in fluid communication with the liquid in the container. The housing comprises a first end having an opening attached thereon the container, a low voltage supplier attached to one wall, a high voltage converter attached to another wall, a voltage contact and a counter electrode, optionally a heat and/or lighting source, a wicking material, and further optionally electronics for voltage regulation. Also disclosed is a process for dispensing liquid using the device.

23 Claims, 2 Drawing Sheets

LIQUID DISPERSION DEVICE

FIELD OF THE INVENTION

Figure 1:
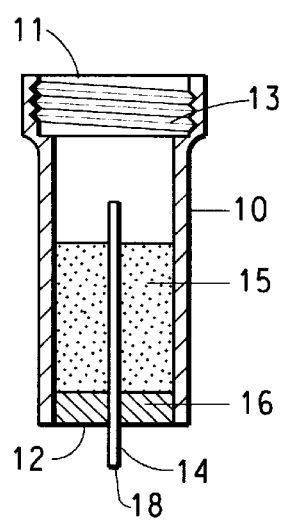

This invention relates to a device for dispersing liquid into vapor and to a process for dispersing or spraying liquid.

BACKGROUND OF THE INVENTION

A device for dispersing a liquid such as, for example, air freshening device in which there is a slow release of vapor into air from a liquid is well known in the art. See, e.g., U.S. Pat. Nos. 2,942,090; 3,780,260; 4,084,079; and 6,478,440. However, current devices rely on evaporation of the liquid from a wick and have the disadvantages of depleting the liquid at an uneven rate and composition, evaporating the more volatile components of the liquid mixture faster and thereby leaving a disproportionately different composition in the liquid from the original composition.

Electrostatic devices for spraying liquids into the air are also well known in the art. See, e.g., U.S. Pat. No. 5,810,265; and EP patent application 0 486 198. In such devices, liquid delivered to a point of high electric potential is drawn out by electrostatic forces into ligaments which break up into fine electrically charged droplets. The liquid is typically delivered to the point of high electric potential by a non-mechanical means such as capillary rise in a small diameter tube or by wicking. Under conditions in which mass transfer by formation of liquid droplets far exceeds the evaporation rate, electrostatic spray devices offer the potential of substantially maintaining a constant liquid composition during the course of dispersing the liquid.

However, the known electrostatic spraying devices that rely on passive delivery of liquid from the reservoir to the high voltage region (by capillary rise or wicking) lack ruggedness. Furthermore, the voltages required for producing electrostatic spraying using the known devices are above 5,000 V and frequently above 10,000 V. At these voltages in air, it is difficult not to produce a Townsend or glow discharge.

Therefore, it is highly desirable to derive a mass transfer device that disperses liquid into a vapor while substantially maintaining the liquid composition at the original composition over the useful life of the device. An advantage of the invention is the range of composition of the liquid to be dispensed can be extended and the composition is not substantially altered for a prolonged period of time.

SUMMARY OF THE INVENTION

Accordingly, the invention comprises a device that can be used as an electrospray device for dispersing liquids into a vapor phase that comprises a container, a capillary device, and a housing. The container has an open end that is connected to the capillary device and comprises a liquid. The capillary device comprises a substantially tubular member having a first end and an opposing end; the first end is secured to the open end of the container; the opposing end has extended therethrough a substantially tubular capillary structure having a capillary tip; the capillary structure is within and coaxially aligned with the substantially tubular member; and the capillary structure is in fluid communication with the liquid in the container. The housing comprises a first end having an opening attached thereon said container, a second end opposing said first end, a first wall having attached thereon a low voltage supplier, a second wall having attached thereon a high voltage converter, a high voltage contact, a counter electrode, optionally a heat and/or lighting source, and further optionally a wicking material. The capillary device is coaxial with the first wall and the second wall. Optionally, the housing may contain control circuitry to turn the high voltage supply on/off or to regulate the high voltage.

Also provided is a process for dispensing a liquid in which the process comprises attaching a capillary device to a container to produce a capillary-container, attaching the capillary-container to a housing, and applying an electrical current to the housing wherein the container, capillary device, and housing can be the same as those disclosed above.

BRIEF DESCRIPTION OF DRAWINGS

FIG. 1 is a cross section of a capillary device for use in accordance with this invention;

FIG. 2A is a cross section of the container with a vent at the top and a capillary structure protruding from the bottom.

FIG. 2B is a similar configuration but with an inner plastic bag (bladder) capable of collapsing as the liquid level diminishes, a preferred device.

FIG. 3 is a cross section demonstrating how the container device might fit into a device for providing a high voltage contact and a counter electrode.

FIG. 4 is a cross section demonstrating a preferred embodiment of the invention which shows that the container fits snuggly into the housing and shows a high voltage contact and a counter electrode.

DETAILED DESCRIPTION OF THE INVENTION

FIG. 1 shows a capillary device that comprises a substantially tubular member 10 having a first end 11 and an opposing end 12. The substantially tubular member has an outer surface, which is generally cylindrical, and an inner surface. The first end, preferably a press fit locking mechanism or threaded locking mechanism, can be secured to the open end 31 of the container 30. The open end 31 preferably has a shape that locks into the first end of the tubular member 10 when pressed together or has an externally threaded portion for easy connection to, by and with an internally threaded connector 13 such that the connection of the tubular member 10 makes a secure and leak proof seal with the container 30. The substantially tubular member 10 can be made from any material but is preferably made with a polymer or plastic such as polypropylene, polyethylene, polybutylene, polyethylene teraphthalate, nylon, and the like or from a metal.

The opposing end of the substantially tubular member 10 has extended therethrough a substantially tubular capillary structure 14 having a capillary tip 18. Capillary structure 14 is coaxial with the tubular structure 10 and can be in fluid communication with liquid 35 of container 30. The tubular capillary structure 14 can be made from a variety of materials. It is preferred that it be made from an electrically conductive material such as, for example, metal; metal coated fused silica; carbon; a polymer comprising a conductive material such as graphite or metal, or a conductive polymer such as polyanaline and combinations thereof. Alternatively, it can be made with any materials such as, for example, fused silica, such that when a high voltage is directly applied to the liquid in container 30 thereby transferring the potential to the tip of the capillary device 14 by means of the electrical conductivity of the liquid.

The inner diameter of the substantially tubular capillary structure is preferably between 40 and 350µ and more preferably between about 50 and about 150µ. The outer diameter is preferably between 70 and 1500µ and more preferably between 100 and 500µ. However, a wider range is possible as the applied voltage, the spacing between the electrodes, the characteristics of the solution to be dispersed or dispensed, and the difference between the inner and outer diameter of the member can be varied over a substantially wide range.

The capillary structure 14 is fixedly inserted within and coaxially aligned with the substantially tubular member 10. Any length of the capillary device can be used so long as the length can accommodate the container 30. The capillary structure is sealed (reference numeral 15) by means of a polymeric material from which the substantially tubular structure is composed or with epoxy resin, or by other means that produces a leak proof seal. The seal may be made with electrically conductive material or be made externally conductive by means of metal, metal surface coatings, carbon black, or by other means that provide a means of applying a voltage to the opposing tip 12 and/or capillary structure 14.

As disclosed above, a sealer 15 can be used inside the substantially tubular member. Any sealer that can fixedly secure the capillary structure within the substantially tubular member can be used. The sealer can also be a semi-solid fluid or electrically conductive such that, upon the application of voltage, current is carried through or along the sealer to the conductive capillary tubular member. Suitable sealers include, but are not limited to, the polymeric material from which the substantially tubular member 10 is made, epoxy resins, metal- or carbon black- or graphite- containing epoxy resins, metals, and combinations of two or more thereof.

To fixedly secure the capillary structure or sealer or both within the substantially tubular member, a stopper 16 such as, for example, a rubber or polymer septum, can be used. Capillary device 14 extends through end 12 with a tip 18 protruding into opening. Tip 18 can be merely protruding or about 0.1 to about 5 mm outside end 12. Optionally, a cap 16 can be used to securely hold the capillary 14 in place and may be conductive to provide a path for applying voltage or ground potential to 14. The cap may be made of any material such as metal or polymer that can provide a leak-tight connection with the tubular structure 10 and with the capillary 14. The capillary and cap may also be a single molded, cast, or machine made structure.

Figures 2A, 2B:
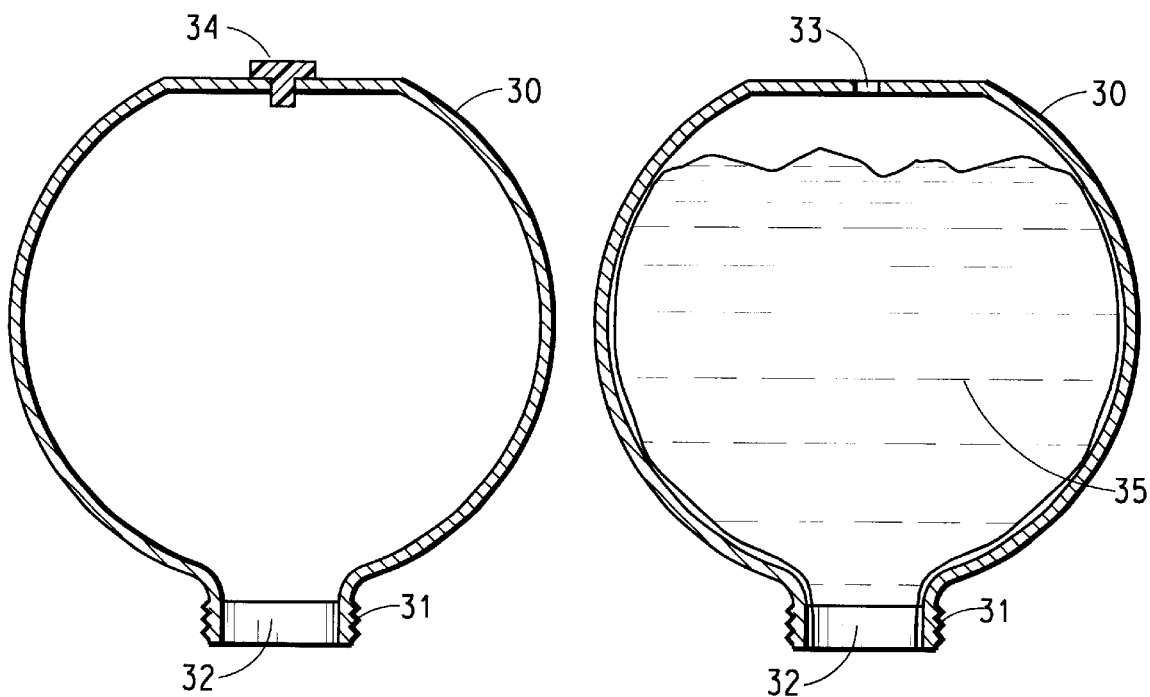
Figure 3:
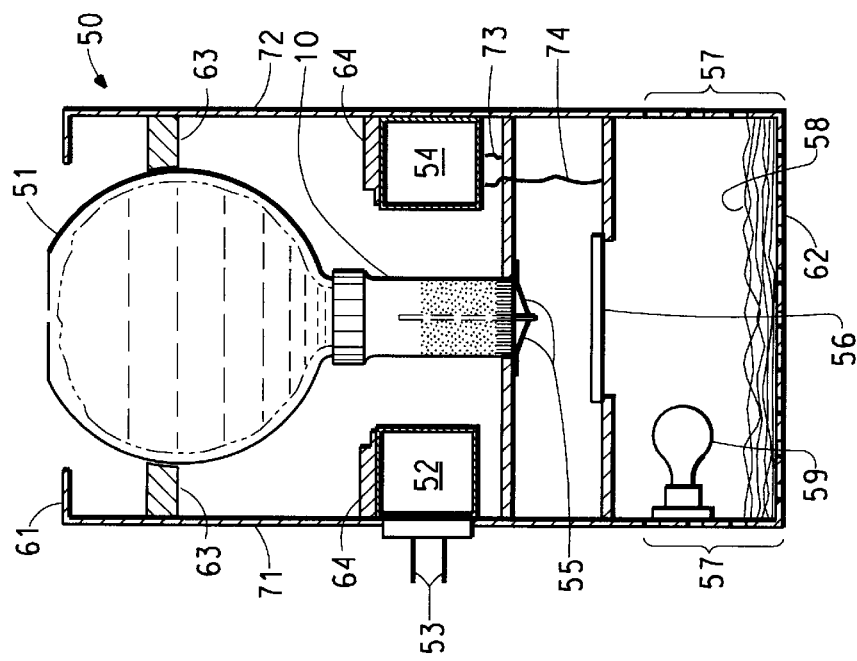

Referring to FIG. 2A and FIG. 2B, a preferred container 30 is illustrated. Container 30 can be any conventional vessel, bottle, or similar device and can be sealed with a closure or cap 32. A preferred container is a rounded bottle having an open end 31 that is preferably eternally threaded or has a press-fit connection for easy connection to the capillary structure disclosed above. The container also has a vent 33, which can be at any location of the container and is preferably at the opposing end 21 to the open end of the container. Vent 33 can be sealed with a stopper 34 such as, for example, a rubber or polymeric septum, or by an adhesive tape or, if an inner polymeric bladder is used, need not be sealed.

Within container 30, there is a liquid 35. Any liquid that has utility as a fragrance, air freshener, mold or mildew inhibitor, disinfectant, air purifier, aromatherapy, antiseptic, insecticide, insect attractant, calibrant for mass spectrometry and other similar uses. The liquid preferably has a volume resistivity of from $10^4$ to $10^{12}$ ohm cm, more preferably a volume resistivity of between $10^5$ and $10^9$ ohm cm. It is also preferably to add a substance such as, for example, an acid, a base, or a salt or combinations or two or more thereof to alter the resistivity of the liquid to fall within the desired range. The liquid also preferably has a viscosity measured at 20° C. of between about 0.1 and about 20000 mPa·s and more preferably 0.1 to 8000 mPa·s. Viscosity adjusting agents such as, for example, ethanol, isopropyl alcohol, glycerol, acetic acid, propanoic acid, water and the like or combinations of two or more thereof can be added to adjust the viscosity of the liquid to a desired range. The liquid preferably has a surface tension between about 15 and 75 dyne/cm. The liquid is preferably an air freshener, a disinfectant, a deodorizer, a mold/mildewcide or an insecticide solution which is electrosprayed by the device of the invention into a room, corridor, air handling system, basement, etc., or a solution containing compounds used as reference materials for electrospray mass spectrometry, or pheromones, steroids, and carbohydrates. The term "electrospray" used herein, unless otherwise indicated, refers to an electrostatic liquid spray that operates below the potential for a corona electric discharge and disperses droplets of liquid from ligands formed at the tip of one or more so called Taylor cones, as well known to one skilled in the art.

Figure 4:
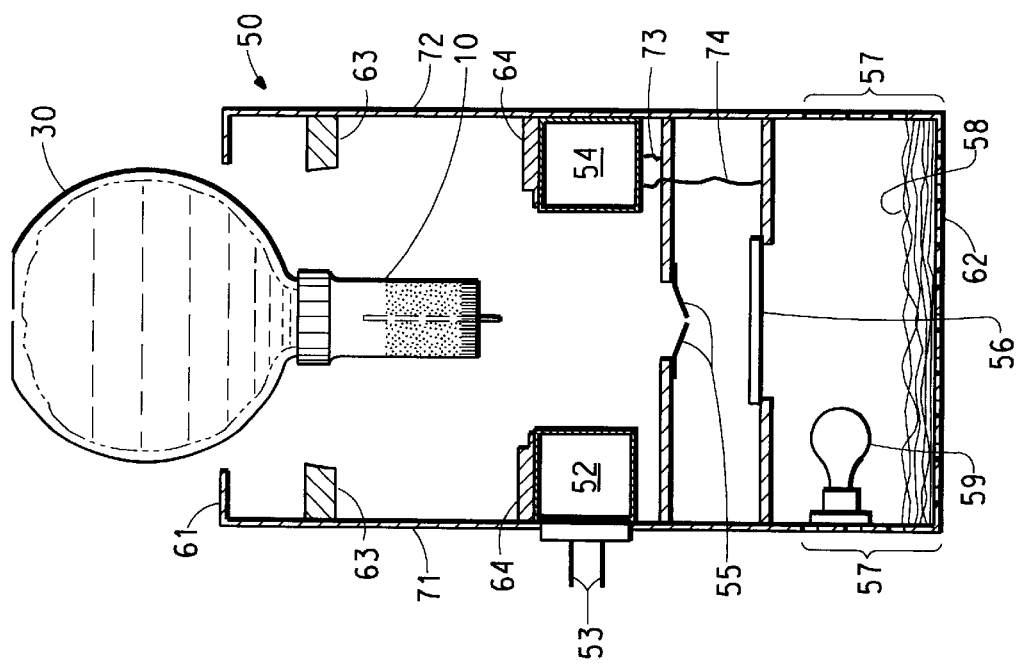

Container 30 can be rested snuggly in or partially in housing 50, through opening 51 as shown in FIG. 4. The housing can be round, rectangular, square, or any shape so long as container 30 can fixedly and snuggly rest within opening 51. A manual releasing locking mechanism holds the container in place even when the housing is inverted. This mechanism can be one or more wall(s) making up opening 51 which has an opening to accommodate a portion of the container 30 or protrusion 63 or 64 that holds 30 in place. Housing 50 comprises an end 62 opposing the opening 51 along the other end 61, a first wall 71, and a second wall 72. The distance between 71 and 72 can be any length as long as it can accommodate the container, a low voltage supplier 52 on one wall with low voltage input 53, and a high voltage converter or housing 54 on another wall. The low voltage source for the high voltage may be either AC or DC and can be provided through house current (120 or 220 V AC) or by a battery. Likewise, the high voltage can either be AC or DC. High voltage housing 54 can comprise a circuit that limits the current flow at high voltage to less than about 100µ amps, a device to convert low voltage to high voltage such as, for example, a transformer. Because such high voltage converting means is well known to one skilled in the art, the description of which is omitted herein for the interest of brevity. Either the low or high voltage device can contain electronics that turn the system on/off or regulate the output voltage. The control electronics can be timers, sensors, manual switches, and the like. The opposing end 12 or capillary structure 14 of substantially tubular structure 10 when fixed snuggly on housing 50 makes contact with an electrical circuit to the high voltage converter. In the preferred configuration, high voltage is supplied to the capillary tubular structure 14 by means of a metal contact 55, which serves as voltage/ground contact and is connected to high voltage converter 54 by wire 73. The capillary tip is in electrical contact with the voltage/ground contact when securely fitted into the housing.

The opposing end 12 of the capillary tubular structure 14 becomes one electrode of the high voltage circuit and a counter electrode 56, connected to high voltage converter 54 through wire 74, lies a distance of between about 1 to about 50 mm, more preferably from 5 to 25 mm, from the opposing end 12. The distance of the electrodes from each other can be a parameter that determines the optimum voltage required to initiate electrospray. The distance between the tip 18 and the counter electrode 56 is most preferably 5 to 20 mm. The high voltage contact generally makes a connection with opposing end 12 to provide electrical contact to the capillary tip 18. The distance between tip 18 and the counter electrode 56 is in the range of from about 1 to about 50 mm and more preferably between 5 and 20 mm. The counter electrode can be a conductive metal and can be almost any smooth structure lying between a wire and a planar surface. The preferred configuration of the counter electrode 56 is a ring structure in which the center is open. Counter electrode 56 can serve as alternative voltage/ground contact.

Counter electrode can also serve as a heater to aid evaporation of any liquid that accumulates on or near electrode 56. An optional lighting source 59 can be present in the housing and any heat emitted from the optional heater or light source can aid evaporation of any accumulated liquid which is than removed through perforated wall 57.

It is highly desirable that the composition of the liquid in container 30 does not change appreciably even after continuous spraying for as much as 30 days or longer. During evaporation, the most volatile components are dispersed at a faster rate than less volatile components. To the contrary, electrospray can dispense all components in a mixture at an equal rate.

Wishing not to be bound by theory, in the off position, evaporation is minimized by the force of the liquid surface tension acting to minimize the liquid surface area exposed to air. A flat smooth surface at the capillary tip minimizes evaporation so that the liquid dispersed by the electrospray process is greater than 10 times that dispersed by evaporation and preferably at least 50 times that of evaporation, and for some solutions more than 1000 times the evaporation rate. Electrospray relies on a balance of several forces. Because the reservoir of liquid is above the capillary tip from which the liquid is sprayed, gravity acts as a low-pressure pump aiding the force of capillary rise (a force dependant on the surface tension of the liquid) to supply liquid to the capillary structure tip. Countering this force is the surface tension of the liquid that acts inward to minimize the area of the liquid exposed to air. In a properly balanced system the liquid can travel to the tip of the capillary structure but instead of exiting the capillary forms a concave meniscus just inside the capillary structure tip. Therefore, the system is preferably so designed that the force of gravity that the liquid within the capillary structure experiences is less than the force of surface tension per unit area at the tip of the capillary structure and acting to keep the liquid within the tip. At the capillary tip, the force due to surface tension is directed inward whereas the force of gravity is directed downward or outward from the liquid. Surface tension ($\gamma$) of a liquid can be approximated by measuring the capillary rise of the liquid in a tube using the equation $\gamma=\frac{1}{2}\rho grh$ where $\rho$ is the liquid density, g is the force constant for gravity, r is the radius of the capillary and h is the height of the liquid above the capillary opening. At the balance point of the two forces, $\gamma(2\pi r)=\rho h(\pi r^2)g$. Thus, in the downward configuration used here, the height of the liquid above the capillary exit tip and/or the radius of the capillary tube is preferably kept small so that the force exerted by gravity does not overcome the surface tension force. In this application, $\lambda>\frac{1}{2}\rho grh$.

The balance of forces discussed above, which maintains the liquid just inside the outlet tip 18 of the capillary, can be modified by applying an electric field between the capillary tip of structure 14 and a counter electrode 56. The electric field induces ions to migrate to the liquid surface. The attractive electrostatic force between the ions at the liquid surface and the counter electrode causes the liquid to move out of the tube into a conical shape and spray droplets into the surrounding air from thin liquid columns extending from the tip of the liquid cone. Once the electric field is turned off, the surface tension again is the dominating force and the liquid withdraws inside the capillary tip.

Also wishing not to be bound by theory, in a device using a capillary the reservoir preferably has a means of maintaining the vapor pressure above the liquid in the reservoir that is equal to the atmospheric pressure outside the reservoir. Otherwise, this pressure difference can overcome the surface tension force and cause liquid to either drain into the reservoir or out from the reservoir. This can be prevented by equalizing the pressure differential inside and outside the container using a vent 33 above the liquid surface. Leakage of liquid from vent 33 can be prevented by sealing the vent opening with a stopper 34, as well as the capillary opening or tip 18, until the device is ready to use, or by enclosing the liquid inside the container in a thin plastic bag (or bladder) such as, for example, polypropylene or polyethylene that collapses as the liquid in the reservoir is depleted, similar to the method used with baby bottles. The plastic bag, thus, prevents the liquid from leaking through the vent hole.

The exit tip 18 of the capillary structure 14 can be a variety of shapes so long as there are no sharp points or edges that generate a gaseous electric discharge. The preferred tip shape is flat (planar), and cut to about a 90° angle to the axis of the capillary. In this configuration, the surface area of the liquid can be minimized which, in turn, minimizes evaporation. In addition, the voltage difference between initiation of electrospray with dispersion of liquid droplets and initiation of a gaseous discharge is maximized. Cutting the capillary tip at an angle may have a reduced voltage range between initiation of electrospray and initiation of a gaseous electrical discharge. It is also possible to use a wide bore tube that tapers to a smaller opening of between 25 and 200$\mu$ inner diameter.

An example of this geometry might be fused silica heated and pulled to reduce the opening at the tip.

Further wishing not to be bound by theory, thin walled capillary structure 14 with a narrow diameter can initiate electrospray at a lower voltage than thick walled structure 14 with a larger diameter. At either extreme, the voltage difference can be reduced between initiation of electrospray and gaseous electrical breakdown to produce a discharge.

The inner diameter can be one of several parameters that determine the rate of liquid that is sprayed into air. For this application, internal diameters below about 40$\mu$ may disperse too little liquid and those above about 350$\mu$ may spray at such a high rate that condensation of the liquid becomes difficult to control. Tapered tips can produce a stable spray at diameters as small as 25$\mu$. The larger the outer diameter, the higher voltage may be required to initiate a discharge. However, specifying a unique range of outer diameters for this application can be difficult the distance between the electrodes, the viscosity and resistivity of the liquid, and the voltage applied can be altered to produce a stable spray over a wide range of outer diameters. In general, the outer diameter is preferably less than 1 mm but larger than, or equal to, the inner diameter by about twice the wall thickness. The length of the capillary structure is generally for convenience of construction. Thus, a capillary structure as short a 1 mm and as long as 100 mm can be made suitable.

In all configurations the maximum evaporation rate in the off position (no voltage applied) is preferably less than $\frac{1}{10}^{th}$ the spray rate that is achieved when the voltage is on, more preferably less than $1/50^{th}$ spray rate or even less than $1/1000^{th}$ the spray rate. Again, wishing not to be bound by theory, the rate of evaporation when the voltage is off is determined by the combination of the surface area of the liquid at the capillary tip that is exposed to atmosphere and the vapor pressure of the liquid. With the voltage off, the surface tension of the liquid causes it to into the tip of the capillary, thus minimizing evaporation. The spray rate when the voltage is on is determined by a number of factors which include the inner diameter of the capillary structure, the field strength at the capillary tip 18, the conductivity of the liquid, and the viscosity of the liquid. When the voltage is on, the electric field causes the to protrude from the tip in a cone shape with liquid ligament(s) extending from the tip producing fine droplets. The mass of the liquid per unit time dispersed by droplet formation under almost all electrospray conditions is >50 times and often >1000 times the mass of the liquid dispersed by evaporation from the capillary tip when the voltage is off. The fine droplets produced in the electrospray process greatly increase the surface area of the liquid that is exposed to atmosphere, which in turn greatly increases the rate of liquid evaporation during the electrospray process. Thus, when the voltage is off, little liquid evaporates from the small liquid surface exposed to atmosphere. However, when the voltage is on and fine drops are being dispersed by the electrospray process, larger amounts of liquid are dispersed as vapor because of the greatly increased liquid surface exposed to atmosphere. Factors that affect the rate of spray are the inner diameter of the capillary structure, the field strength at the tip 18 of the capillary structure, and the conductivity and viscosity of the liquid being sprayed. In practice, the rate of liquid to dispersion by electrospraying can be controlled by the inner diameter of the capillary structure and the voltage applied between the capillary tip and the counter electrode. Minimizing the inner diameter and the voltage applied will minimize the amount of liquid dispersed while maximizing the inner diameter of the capillary structure within the claimed range and use of a higher voltage will maximize the amount of liquid dispersed. The device is capable of, but not limited to, dispensing a liquid at a constant rate per day, with a deviation of less than plus or minus 20%, over a period of at least, 10 days, preferably at least 20 days, and more preferably at least 30 days. The device is also capable of, but not limited to dispensing a liquid such that the composition of the liquid if sprayed for the time period disclosed above does not change by more than 10% from the starting composition. Depending on the configuration of the device, the spray rate can be, for example, between 0.2 and 10, preferably 0.2 and 5 grams per day when operated continuously. For fragrance delivery, for example, the preferred spray rate is between 0.4 and 1.5 grams/day.

At a spray rate of 1 gram per day, the container would provide for one month of continuous spraying if it contained approximately 30 grams of fragrance. This assumes a constant spray rate regardless of the level of liquid in the container. This is a particular advantage of the gravity feed approach. The force of gravity acts as a pump to aid surface tension (capillary rise) supply liquid to the tip, but in the devices described here does not overcome the surface tension that prevents the liquid from spilling from the capillary structure. The spray rate is determined by the characteristics of the liquid being sprayed and the field at the tip of the electrode. Thus, so long as the combined forces of capillary rise and gravity acting on the liquid column can supply as much liquid as can be electrosprayed to the capillary tip, then the spray rate remains essentially constant as the container is emptied.

A high electric field is applied to the liquid at the capillary exit tip 18 by applying a voltage potential across contact 55, and thus also tip 18, and the counter electrode 56. Preferably, the voltage supply operates at a potential in a range of about 1.5 to about 10 kV, more preferably 2 to 5 kV, and most preferably 2 to 4 kV. The electric field applied to the liquid surface at the tip 18 may be continuous or intermittent. The device may be operated intermittently by a manual on/off switch, or automatically using a timing or sensor device or remotely. In particular the on/off timing of the spray cycle may be adjusted to provide a level of dispersion (e.g. fragrance) that is appropriate for room size or application. In addition, multiple units can operate together so that in the case of fragrance delivery, for example, one fragrance could be delivered in the morning, another in the afternoon and none at night. This can be accomplished by having multiple containers for holding liquid, each with the capillary structure, and alternating applying electric potential between each of the capillary structures and the counter electrode. In the case of insecticide or disinfectant, it may be desirable to only deliver at night. In this case, the device would be set to provide high voltage only during the desired time interval or by using a sensor that turns the voltage on only when dark. As discussed above, the low voltage source for the high voltage may be either AC or DC and can be provided through house current (120 or 220 V AC) or by a battery and the high voltage can either be AC or DC. In either case, when the voltage is applied, liquid is drawn from the tube and dispersed as fine droplets into the air. When the voltage is switched off, the liquid withdraws to the open face of the capillary structure.

This invention also comprises means of applying heat to the area of condense onto the counter electrode 56. The heat source can be a passing electric current through a resistive device that serves as the counter electrode in order to heat the electrode. The heat source can be one near the counter electrode such as the lighting source 59. Alternatively, a high surface area wicking material such as, for example, cotton or a thin woven sheet made of polymeric material can be made in contact with counter electrode 56 to wick condensed liquid to a large surface area for faster evaporation. Also alternatively, as shown in FIG. 3 and FIG. 4, a wicking material 58 can be placed at the bottom of housing 50 to aid evaporation of condensed spray by providing a large surface area and to prevent condensate from exiting the device.

Preferably container 30, as described previously, holding liquid 35 and has an air vent 33, has a capillary structure to deliver the liquid in a downward direction providing an electric contact at high voltage in housing 50. This container can be used as a refill. The high voltage housing 54 includes a circuit that limits the current flow at high voltage to less than about 100$\mu$ amps, a device to convert low voltage to high voltage that may be as simple as a transformer, a counter electrode and a means of providing electrical contact with the container described above. Housing 50 also contains vented wall 57 for dispersion of vapor and for heat removal and may contain wicking material 58 and a heating source which may double as a nightlight 59. Optionally, the housing may contain electronics for control of the high voltage.

The invention also provides process for dispersing a liquid from a container or reservoir. The process comprises attaching a capillary device to a container to produce a capillary-container, attaching the capillary-container to a housing, and applying an electrical current to the housing.

The container, liquid, capillary device, and housing can be the same as those disclosed above. The electrical current can be supplied by either direct current such as a battery or alternate current such as house current (120 or 220 V AC). Low voltage provided by these sources is converted to high voltage by the high current converter in the device disclosed above. As the voltage is applied, liquid is drawn from the capillary structure through tip 18 and dispersed as fine droplets into the air. The rate and timing of liquid dispersion can be altered or controlled by electrical means such as, for example, by using a manual switch, a timer, a voltage output regulator, a variable transformer, a sensor, or a remote device. The dispersion of liquid to the vapor phase can be started and stopped at will or even disperse different liquid solutions at different times.

The following examples are provided to illustrate, and should not be construed as to unduly limit, the scope of the invention.

EXAMPLES

In the first instance, a simple device was built in which a 1 cm long tubular metal capillary structure with flat smooth ends and having an inner diameter of $100\mu$ and an outer diameter of $230\mu$ was sealed in a polypropylene container using a solvent resistant epoxy. A liquid (6 ml) made up of glycerol, water, methanol, and isopropanol was added through a vent in the top of the container. A DC power supply was used to provide approximately 4000 V to a wire which was a distance of approximately 1 cm from the capillary tube. The capillary tube was grounded to the case of the power supply. With the capillary facing downward, the liquid level being in contact with and above the uppermost opening of the capillary structure, a liquid cone formed at the bottommost capillary opening when the voltage was applied. With the voltage on, the electrospray process was initiated and fine droplets were dispensed into the surrounding air. When the voltage was off, the liquid withdrew into the bottommost tip of the capillary structure. The container with liquid was weighed and then again weighed after 24 hours with no voltage applied. This provided an evaporation rate in grams/hour. This experiment was repeated but the voltage was applied for the 24 hour period during which time electrospray was initiated. This provided the spray rate in grams/hour. The spray rate was found to be about 1800 times the evaporation rate for this mixture under the conditions of this test. The container was again filled with a total of 6 ml of the starting solvent mixture and the voltage was left on until the device dispensed all of the liquid above the uppermost capillary opening (5.5 ml). The remaining ½ ml and ½ ml of the starting solvent mixture was submitted for gas chromatography analysis. Analysis showed no detectable change in solvent composition before and after electrospray.

A later device was made by modification of a commercial evaporative fragrance dispenser. The modification was similar to what is shown in the drawings in FIG. 1–4 without an optional heater or light source and with use of a vent hole in the container. The commercial fragrance solution (8 ml) was added to the container and the container was placed in the holder with the capillary structure facing downward and making electric contact with a metal washer through a painted silver coating on the end of the tubular structure. A second metal washer located approximately 1 cm from the capillary tip acted as the counter electrode. A potential of 3000 V was placed between the two washers generating electrospray conditions. The device was operated for 7 days, dispensing 7 ml of liquid. Gas chromatography/mass spectrometry analysis of the fragrance as received and the fragrance after spraying 7 of 8 ml of fragrance solution showed no differences beyond expected run to run variations (Table I).

A portable device was also made as a demonstrator model. This device was similar in concept to the device described above with the exception that the high voltage was generated from flashlight batteries (3–6 V) using EMCO Q series voltage converters to convert the low voltage to between 2000 V and 5000 V DC, as is well known to one skilled in the art.

The housing for this device was made of clear plastic for viewing purposes and the counter electrode was a wire rather than a ring structure. This device was turned on and off repeatedly and after periods as long as 6 days either continuously off or continuously on. Other than the need for fresh batteries, the device never failed to operate over the 3 month period of on/off operation.

The results shown in Table I below are GC/MS comparison of initial fragrance composition before and after electrospraying. Initial solution volume 8 ml, final solution volume 1 ml. The results demonstrate that any variation in relative concentration of components is random with retention time and presumably volatility and within the expected run to run variability for this analysis.

TABLE I

| Ret. Time (min) | Pk. Area Before | Pk Area After |
|---|---|---|
| 1.6 | 308 | 312 |
| 5.5 | 1287 | 1332 |
| 6.9 | 341 | 328 |
| 7.0 | 319 | 333 |
| 7.1 | 388 | 404 |
| 8.1 | 280 | 264 |
| 8.6 | 188 | 168 |
| 8.8 | 427 | 437 |
| 10.1 | 117 | 116 |
| 10.5 | 1428 | 1331 |
| 12.1 | 401 | 399 |
| 13.7 | 500 | 507 |

What is claimed is:

1. A device comprising a container, a capillary device, and a housing wherein said container has an open end that is connected to said capillary device and comprises a liquid;

said capillary device comprises a substantially tubular member having a first end and an opposing end; said first end is secured to said open end of said container; said opposing end has extended therethrough a substantially tubular capillary structure having a capillary tip; said capillary structure is coaxially aligned with said substantially tubular member; and said capillary structure is in fluid communication with said liquid;

said housing comprises a first end having an opening attached thereon said container, a second end opposing said first end, a first wall having attached thereon a low voltage supplier, a second wall having attached thereon a high voltage converter, a counter electrode connected to said high voltage supply, and optionally a lighting source, a wicking material, electronics for voltage regulation, or two or more thereof; and said capillary structure is coaxial with said first wall and said second wall; and the distance from said capillary tip to said counter electrode is in the range of from about 1 to about 50 mm.

2. A device according to claim 1 wherein the distance from said opposing end of said capillary device to said counter electrode is in the range of from about 1 to about 50 mm.

3. A device according to claim 1 wherein said liquid has a viscosity in the range of 0.1 to 20000 mPa·s at 20° C.

4. A device according to claim 1 wherein said liquid has a volume resistivity of between $10^4$ and $10^{12}$ ohm cm.

5. A device according to claim 1 wherein said liquid has a surface tension in the range of 15 and 73 dyne/cm.

6. A device according to claim 1 wherein said substantially tubular member is made from a polymer, plastic, or metal.

7. A device according to claim 6 wherein said capillary structure is made from an electrically conductive material, a polymer comprising a conductive material, a conductive polymer, fused silica, or metal coated fused silica.

8. A device according to claim 7 wherein said capillary structure has an outer diameter in the range of 0.07 to 1.5 mm.

9. A device according to claim 7 wherein said capillary structure has an inner diameter in the range of 0.04 to 0.35 mm.

10. A device according to claim 1 wherein said capillary structure tip is flat (planar) and cut to about 90° angle to the axis of said capillary structure.

11. A device according to claim 1 wherein said device is capable is of dispensing said liquid at a constant rate per day over a period of at least 10 days.

12. A device according to claim 11 wherein rate is in the range of about 0.2 to about 10 g per day.

13. A device according to claim 11 wherein the chemical composition of said liquid does not change by more than 10% from the starting chemical composition.

14. A process for dispensing liquid comprising attaching a capillary device to a container to produce a capillary-container, attaching said capillary-container to a housing, and applying an electrical current to said housing wherein said container has an open end that is connected to said capillary device and comprises a liquid;

said capillary device comprises a substantially tubular member having a first end and an opposing end; said first end is secured to said open end of said container; said opposing end has extended therethrough a substantially tubular capillary structure having a capillary tip; said capillary structure is coaxially aligned with said substantially tubular member; and said capillary structure is in fluid communication with said liquid;

said housing comprises a first end having an opening attached thereon said container, a second end opposing said first end, a first wall having attached thereon a low voltage supplier, a second wall having attached thereon a high voltage converter, a high voltage contact, a counter electrode, optionally a lighting source, a wicking material, and further optional electronics for voltage regulation; and said capillary device is coaxial with said first wall and said second wall; and the distance from said capillary tip to said counter electrode is in the range of from about 1 to about 50 mm.

15. A process according to claim 14 wherein said liquid is fragrance, air freshener, mold or mildew inhibitor, disinfectant, air purifier, aromatherapy, antiseptic, insecticide, insect attractant, or calibrant for mass spectrometry.

16. A process according to claim 15 wherein said electrical current produce a high voltage in the range of 2 to 10 kV.

17. A process according to claim 16 wherein the distance from said opposing end of said capillary device to said counter electrode is in the range of from about 2 to about 50 mm.

18. A process according to claim 17 wherein said capillary structure is made from an electrically conductive material, a polymer comprising a conductive material, a conductive polymer, fused silica, or metal coated fused silica.

19. A process according to claim 17 wherein said capillary structure has an outer diameter in the range of 0.07 to 1.5 mm.

20. A process according to claim 17 wherein said capillary structure has an inner diameter in the range of 0.04 to 0.35 mm.

21. A process according to claim 20 wherein said capillary structure tip is flat (planar) and cut to about 90° angle to the axis of said capillary structure.

22. A process according to claim 16 wherein said substantially tubular member is made from a polymer, plastic, or metal.

23. A process according to claim 15 wherein said voltage produces a given field strength having a weight of liquid dispensed more than 10 times greater than the weight of liquid that evaporates over an equal time period without said voltage.

* * * * *

UNITED STATES PATENT AND TRADEMARK OFFICE
CERTIFICATE OF CORRECTION

PATENT NO. : 6,729,552 B1
DATED : May 4, 2004
INVENTOR(S) : McEwen Charles Nehemiah, Herron William J. and McKay Richard G.

It is certified that error appears in the above-identified patent and that said Letters Patent is hereby corrected as shown below:

Column 11,
Line 24, delete the following word "is" which appears after the word "capable".

Signed and Sealed this

Twenty-eighth Day of December, 2004

JON W. DUDAS
*Director of the United States Patent and Trademark Office*